US00PP25872P2

(12) United States Plant Patent
Wood

(10) Patent No.: US PP25,872 P2
(45) Date of Patent: Sep. 8, 2015

(54) ***VIBURNUM* PLANT NAMED 'SMVCB'**

(50) Latin Name: *Viburnum carlesii*
Varietal Denomination: SMVCB

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 38 days.

(21) Appl. No.: 13/987,826

(22) Filed: Sep. 7, 2013

(51) Int. Cl.
*A01H 5/08* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — C. A. Whealy

(57) ABSTRACT

A new and distinct cultivar of *Viburnum* plant named 'SMVCB', characterized by its compact, upright and somewhat outwardly spreading plant habit; vigorous growth habit; freely branching habit; large inflorescences with numerous fragrant light pink to white-colored flowers; and good container and garden performance.

2 Drawing Sheets

Botanical designation: *Viburnum carlesii.*
Cultivar denomination: 'SMVCB'.

BACKGROUND OF THE INVENTION

The present invention relates to a new and distinct cultivar of *Viburnum* plant, botanically known as *Viburnum carlesii* and hereinafter referred to by the name 'SMVCB'.

The new *Viburnum* plant is a product of a planned breeding program conducted by the Inventor in Grand Haven, Mich. The objective of the breeding program is to develop new compact *Viburnum* plants with unique and attractive leaf and flower coloration.

The new *Viburnum* plant originated from an open-pollination during the summer of 2006 of *Viburnum carlesii* 'Compactum', not patented, as the female, or seed, parent with an unknown selection of *Viburnum carlesii* as the male, or pollen, parent. The new *Viburnum* plant was discovered and selected by the Inventor in 2009 as a single flowering plant from within the progeny of the stated open-pollination in a controlled environment in Grand Haven, Mich.

Asexual reproduction of the new *Viburnum* plant by softwood cuttings in a controlled environment in Grand Haven, Mich. since June, 2009 has shown that the unique features of this new *Viburnum* plant are stable and reproduced true to type in successive generations of asexual reproduction.

SUMMARY OF THE INVENTION

Plants of the new *Viburnum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMVCB'. These characteristics in combination distinguish 'SMVCB' as a new and distinct *Viburnum* plant:

1. Compact, upright and somewhat outwardly spreading plant habit.
2. Vigorous growth habit.
3. Freely branching habit.
4. Large inflorescences with numerous fragrant light pink to white-colored flowers.
5. Good container and garden performance.

Plants of the new *Viburnum* can be compared to plants of the female parent, 'Compactum'. Plants of the new *Viburnum* differ from plants of 'Compactum' in the following characteristics:

1. Plants of the new *Viburnum* are easier to root and grow than plants of 'Compactum'.
2. Plants of the new *Viburnum* are more uniform and have better container performance than plants of 'Compactum'.

Plants of the new *Viburnum* can be compared to plants of the *Viburnum carlesii* 'Spiro', disclosed in U.S. Plant Pat. No. 24,251. Plants of the new *Viburnum* differ from plants of 'Spiro' in the following characteristics:

1. Plants of the new *Viburnum* are more compact than plants of 'Spiro'.
2. Flowers of plants of the new *Viburnum* are not as fragrant as flowers of plants of 'Spiro'.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical plant of 'SMVCB' grown in an outdoor nursery.

The photograph on the second sheet is a close-up view of an inflorescence of 'SMVCB'.

DETAILED BOTANICAL DESCRIPTION

The aforementioned photographs and following observations, measurements and values describe plants of the new

*Viburnum* grown in ground beds and one-gallon containers during the summer in an outdoor nursery in Grand Haven, Mich. and under cultural practices typical of commercial *Viburnum* production. Plants were one year old when the photographs and the description were taken. In the description, color references are made to The Royal Horticultural Society Colour Chart, 2001 Edition, except where general terms of ordinary dictionary significance are used.

Botanical classification: *Viburnum carlesii* 'SMVCB'.

Parentage:

*Female, or seed, parent.*—*Viburnum carlesii* 'Compactum', not patented.

*Male, or pollen, parent.*—Unknown selection of *Viburnum carlesii*, not patented.

Propagation:

*Type.*—By softwood cuttings.

*Time to initiate roots, summer.*—About 40 days at 24° C.

*Time to produce a rooted young plant, summer.*—About six months at 24° C.

*Root description.*—Fine to thick; white and brown in color.

*Rooting habit.*—Freely branching; dense.

Plant description:

*Plant and growth habit.*—Deciduous perennial shrub; compact, upright and somewhat outwardly spreading plant habit; vigorous growth habit.

*Branching habit.*—Freely branching habit with numerous primary lateral branches developing per plant; pinching (removal of terminal apices) will enhance lateral branch development.

*Plant height.*—About 45 cm.

*Plant diameter* (*area of spread*).—About 45 cm.

Lateral branch description:

*Length.*—About 35 cm.

*Diameter.*—About 5 mm.

*Internode length.*—About 8.5 cm.

*Texture.*—Pubescent.

*Strength.*—Moderately strong.

*Aspect.*—Erect to about 20° from vertical.

*Color.*—Close to 199A.

Leaf description:

*Arrangement.*—Opposite, simple.

*Length.*—About 12 cm.

*Width.*—About 6.5 cm.

*Shape.*—Ovate.

*Apex.*—Acuminate.

*Base.*—Obtuse.

*Margin.*—Dentate.

*Texture, upper and lower surfaces.*—Pubescent.

*Venation pattern.*—Pinnate.

*Color.*—Developing leaves, upper surface: Close to 137C. Developing leaves, lower surface: Close to 148C. Fully expanded leaves, upper surface: Close to 139A; venation, close to 144A. Fully expanded leaves, lower surface: Close to 148B; venation, close to 145A.

*Petiole.*—Length: About 1 cm. Diameter: About 3 mm. Texture, upper and lower surfaces: Smooth, glabrous. Color, upper and lower surfaces: Close to 146D.

Flower description:

*Flower appearance and arrangement.*—Single salverform flowers arranged in terminal cymes; freely flowering habit with usually about 79 flowers per inflorescence; flowers face upright to outwardly.

*Natural flowering season.*—Flowering commences in the early spring in Michigan; flowers last about two to four weeks on the plant and about two weeks as a cut flower; flowers not persistent.

*Fragrance.*—Fragrant; sweet, pleasant.

*Inflorescence height.*—About 7 cm.

*Inflorescence diameter.*—About 7 cm.

*Flower diameter.*—About 1.2 cm.

*Flower length* (*height*).—About 2 cm.

*Flower buds.*—Length: About 1 cm. Diameter: About 4 mm. Shape: Club-shaped. Color: Close to 155D and 63C.

*Petals.*—Quantity per flower: Five petals in a single whorl. Length: About 5 mm. Width: About 5 mm. Lobe shape: Rounded. Apex: Obtuse. Margin: Entire. Texture, upper and lower surfaces: Smooth, glabrous. Color: When opening, upper and lower surfaces: Close to 155D flushed with close to 63C. Fully opened, upper and lower surfaces: Close to 155D.

*Sepals.*—Quantity per flower: Five sepals in a single whorl. Length: About 2 mm. Width: About 1 mm. Shape: Narrowly lanceolate. Apex: Acute. Margin: Entire. Texture, upper and lower surfaces: Smooth, glabrous. Color: When opening, upper and lower surfaces: Close to 144A. Fully opened, upper and lower surfaces: Close to 144A.

*Peduncles.*—Length: About 2.5 cm. Diameter: About 2.5 mm. Strength: Strong. Texture: Smooth. Color: Close to 137A.

*Pedicels.*—Length: About 4 mm. Diameter: About 1 mm. Strength: Strong. Texture: Smooth. Color: Close to 144A.

*Reproductive organs.*—Androecium: Quantity per flower: About five. Anther shape: Lanceolate. Anther size: About 0.5 mm by 1 mm. Anther color: Close to 2B. Amount of pollen: Moderate. Pollen color: Close to 2B.

*Gynoecium.*—Quantity per flower: One. Pistil length: About 1 mm. Style length: About 0.5 mm. Style color: Close to 144A. Stigma shape: Obtuse. Stigma color: Close to 144A. Ovary color: Close to 144A.

*Fruits.*—Length: About 1 cm. Diameter: About 6 mm. Texture: Smooth. Color: Close to 59A.

Garden performance: Plants of the new *Viburnum* have been observed to have good garden and container performance and to tolerate rain, wind and temperatures ranging from about −10° C. to about 35° C.

Pathogen & pest resistance: Plants of the new *Viburnum* have not been observed to be resistant to pathogens and pests common to *Viburnum* plants.

It is claimed:

1. A new and distinct *Viburnum* plant named 'SMVCB' as illustrated and described.

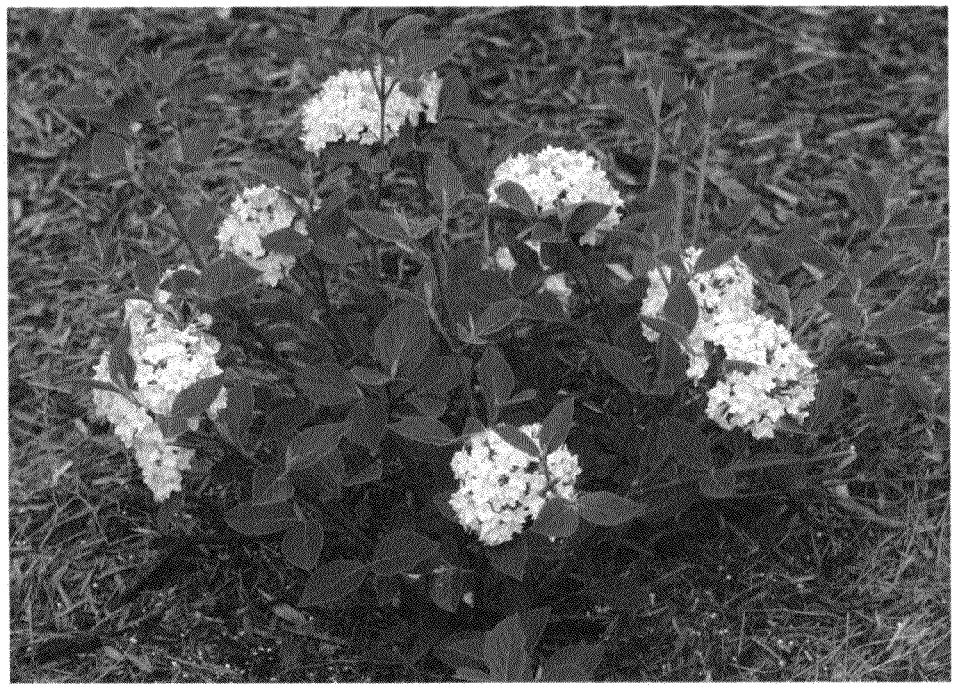

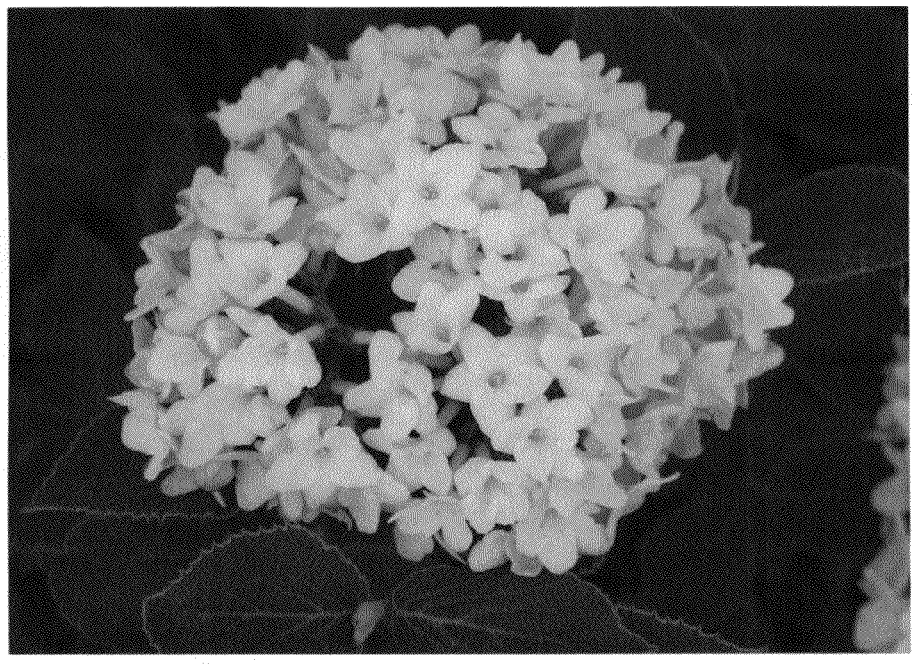

* * * * *